United States Patent [19]

Picard et al.

[11] Patent Number: 4,935,107

[45] Date of Patent: Jun. 19, 1990

[54] PROCESS FOR ELECTROCHEMICAL MEASUREMENT OF THE CONCENTRATION OF OXIDE IONS IN A BATH BASED ON MOLTEN HALIDES

[75] Inventors: Gerard Picard, Fontenay sous Bois; Yves Bertaud, St. Jean de Maurienne; Evelyne Prat, Paris; Michel Leroy, St. Egreve, all of France

[73] Assignee: Aluminium Pechiney, Paris, France

[21] Appl. No.: 106,256

[22] Filed: Oct. 9, 1987

[30] Foreign Application Priority Data

Oct. 17, 1986 [FR] France .................................. 86 14756

[51] Int. Cl.$^5$ .......................................... G01N 27/411
[52] U.S. Cl. ................................ 204/153.16; 204/422
[58] Field of Search ................. 204/1 T, 1 Y, 422, 423

[56] References Cited

U.S. PATENT DOCUMENTS 3,791,954 2/1974 Noda et al. .......................... 204/423
4,639,304 1/1987 Bader et al. ..................... 204/422 X

OTHER PUBLICATIONS

Bard et al., "Electrochemical Methods", John Wiley & Son, Inc., 1980, pp. 316–367.

Primary Examiner—Nam X. Nguyen
Attorney, Agent, or Firm—Dennison, Meserole, Pollack & Scheiner

[57] ABSTRACT

The invention concerns a process and apparatus for electrochemical measurement of the concentration of oxide ions dissolved in a bath based on molten halides. The process is based on impedance measurement at a low current and a low overvoltage, between an indicator electrode, a reference electrode and a counter electrodes. The real value $Z_r$ of the impedance is determined for two frequencies, a low frequency Zr(B) (such as 15–25 Hz) and a high frequency Zr(H) (such as 10–100 kHz); the inverse of the concentration of oxide ions is a linear function of the difference between Zr(B) and Zr(H). This method has a high level of accuracy in the low ranges of concentration of oxide ions.

14 Claims, 3 Drawing Sheets

PROCESS FOR ELECTROCHEMICAL MEASUREMENT OF THE CONCENTRATION OF OXIDE IONS IN A BATH BASED ON MOLTEN HALIDES

TECHNICAL FIELD OF THE INVENTION

The invention concerns a process and an apparatus for electrochemical measurement of the concentration of oxide ions dissolved in a bath based on molten halides. It is applied inter alia to measuring the level of concentration of dissolved oxide in igneous electrolysis baths for the production of aluminium or metals of the rare earth group.

STATE OF THE ART

In industrial cells which operate in accordance with a process for electrolysis of an oxide dissolved in a bath based on molten halides, one of the main concerns of the operator and also the main difficulty is to monitor the proportions of oxide ions in the electrolyte. That is the case in particular in the industry dealing with aluminium or certain rare earth metals (lanthanum and cerium) in which an excess of oxide results in the formation of sludge in the bottom of the crucible, with highly prejudicial consequences in regard to progress of the electrolysis operation, while impoverishment with respect to oxide ions results in a polarisation action, referred to as the "anode effect", which interferes with operation of the cells.

Direct or indirect methods for ascertaining the proportion of oxide and if possible regulating it have already been proposed. Such methods are disclosed in particular in U.S. Pat. No. 4 450 063 (=French No. 2 552 549) (Reynolds), U.S. Pat. No. 4,447,301, JA-Kokai-81/158889 (Sumitomo) and French No. 1 256 640 (Ugine).

DISADVANTAGES OF THE PRIOR ART

Broadly speaking, electrochemical methods for detecting the amount of oxide ions in a molten bath are as follows: potentiometry, voltamperometry and chronoamperometry.

They suffer from certain disadvantages, in particular, in regard to the first, a lack of accuracy and sensitivity, in particular at the levels of concentration of oxide ions of less than 4%, which are used in the Hall-Heroult electrolysis tanks for the production of aluminium.

The last two are generally more sensitive but, the analysis current being relatively high, that gives rise to a substantial amount of gas being given off at the electrodes and, in the case of a consumable electrode (carbon), it results in a substantial alteration in the geometrical properties thereof. Such phenomena severely interfere with the measurements, thus limiting their reproducibility and their degree of accuracy.

In addition, in most cases, the materials used, in particular insulating materials, are highly troublesome, such as for example boron nitride, and are subjected to attack on the part of the molten bath. It is therefore not reasonable from an economic point of view to use consumable detectors. Moreover, such devices are generally insensitive in regard to low proportions of oxide ions, therefore close to the anode effect. Now it has been demonstrated that, in the case of aluminium, it was in that area that the level of current efficiency of the electrolysis operation could reach its maximum values (French patent No. 2 487 386 (=U.S. Pat. No. 4 431 491) and French patent No. 2 581 660, in the name of PECHINEY).

Moreover, electrolysis with a very low level of concentration of oxide is the only one which can be envisaged when the oxide in question is weakly soluble in the molten halide bath: that is the case in particular with neodymium and cerium, lanthanum and yttrium.

Finally, it may be an attractive proposition to detect pollution of the halogenated bath by oxide ions in order to avoid precipitation of the oxides, which interferes with the process: that is the case with tanks for the electrolytic refining of aluminium using the process which is referred to as the "three-layer" process.

The present invention makes it possible to solve those problems but it is also characterised by the adoption of materials which are readily available and which can be economically replaced. Finally, it makes it possible to monitor a large number of cells by means of a single control module, by multiplexing of the signals involved.

SUBJECT-MATTER OF THE INVENTION

The measurement process which forms the basis of the invention is impedancemetry with a low current and a low overvoltage, which, in contrast to all the other electrochemical methods, has the effect of limiting the causes of disturbance, which have been referred to above.

The process is characterised by the succession of the following steps:

(a) a reference electrode, an indicator electrode and a counter-electrode are disposed in a molten halogen-bearing bath, (b) a potential difference is applied between the indicator electrode and the reference electrode, so that the indicator electrode is the location of an anodic electrochemical reaction (oxidation) and the counter-electrode is the location of a cathodic electrochemical reaction, (c) if the electrochemical reaction on the indicator electrode gives rise to gas being given off, the potential difference is so adjusted as to obtain an anodic current density which is at most equal to 10% and preferably at most equal to 2% of the diffusion-limit current density corresponding to the oxide ions in the molten bath, (d) superimposed on the continuous potential of the indicator electrode is a periodic signal of low amplitude, which is adjustable with respect to voltage and frequency, (e) the real value Zr(H) of the impedance for a first, high, frequency of the periodic signal which is at least equal to 500 Hz and then the real value Zr(B) for a second, low, frequency of the periodic signal which is lower than 50 Hz are determined, (f) the proportion of oxide ions in the electrolyte is calculated by applying the relationship:

$$C(O^{-II}) = \frac{A}{\Delta Zr - B}$$

$C(O^{-II})$ being expressed in moles of ions $O^{-II}.cm^{-3}$, $\Delta Zr$ being equal to $Zr(H) - Zr(B)$, A and B being constants obtained by preliminary calibration.

The invention also concerns an apparatus for carrying out the above-indicated measurement process characterised in that it comprises an indicator electrode of an electron conductor or semi-conductor material (carbon, ceramics, metals, metallic compounds), a reference electrode formed by an element or compound involving electron conduction, giving a stable electrochemical potential in the presence of the oxide ions of the molten bath, such as nickel, tungsten, graphite or titanium diboride, and a counter-electrode which may be combined with the reference electrode.

The apparatus further comprises a generator for producing the polarisation potential and the periodic signal of adjustable frequency and voltage and means for processing of the signals received, which are not part of the invention.

DESCRIPTION OF THE INVENTION

Figure 1:
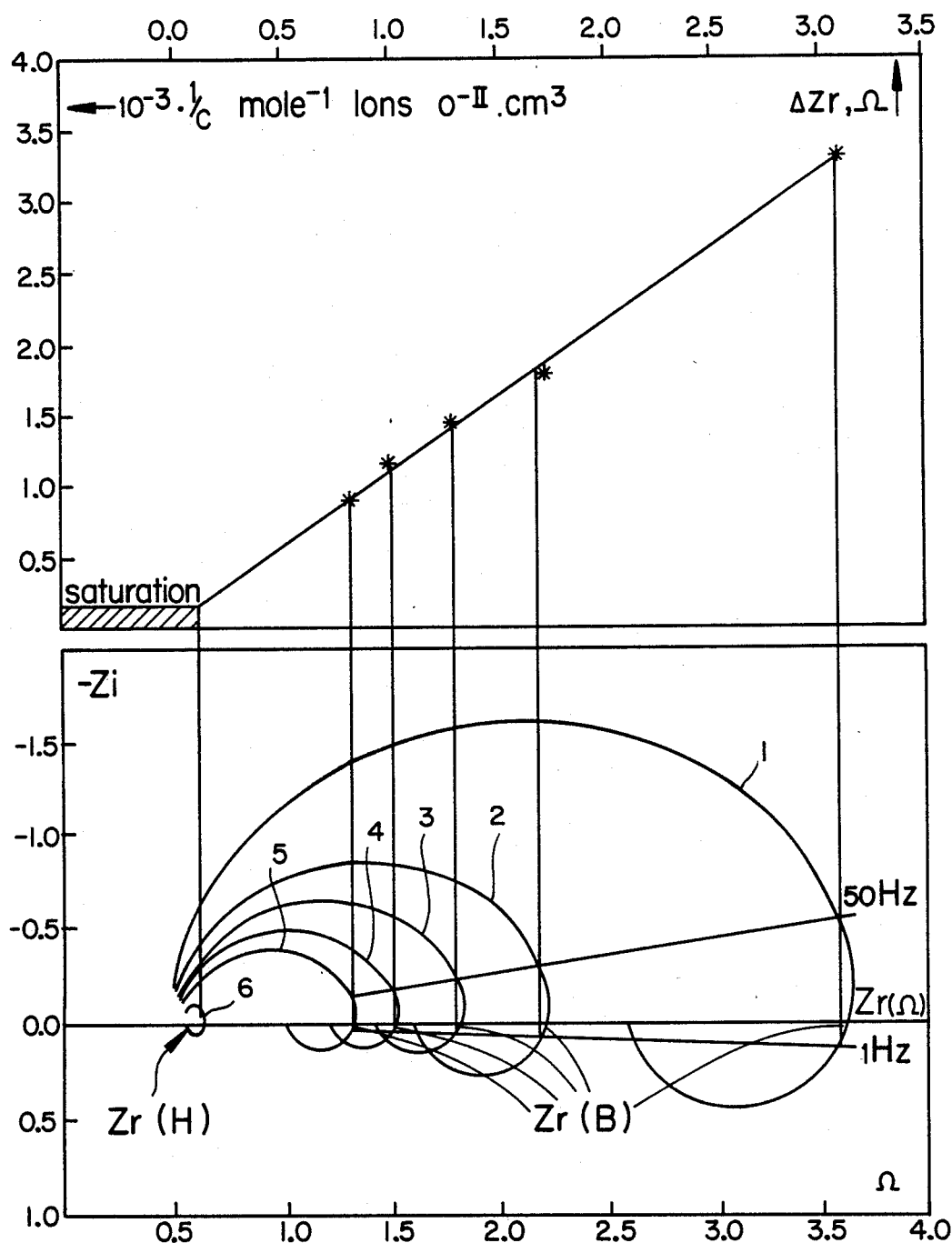
FIG. 1 includes a plot of imaginary impedance versus real impedance for the system described in Example 1, and a plot of the inverse of the oxygen ion concentration versus the difference in real impedance between high and low frequencies, for the system described in Example 1.

For carrying the impedancemetry method according to the invention into effect, the electrodes are firstly disposed in the molten bath, namely the indicator electrode, the reference electrode and the counter-electrode.

The indicator electrode is made of an electron conductor or semi-conductor material selected from:
  carbon in all its current forms and varieties,
  ceramics and cermets such as tin dioxide, nickel or cobalt ferrites and titanium dioboride
  refractory metals such as tungsten or molybdenum,
  noble metals (platinum) or compounds containing same.

The reference electrode is formed by an electron-conductor element or compound which in the presence of the oxide ions in the bath gives a stable electrochemical potential such as tungsten, nickel, graphite, titanium diboride or liquid aluminium.

The counter-electrode which must be of very large surface area with respect to that of the indicator electrode may be for example of graphite or tungsten. The electrodes must also be formed from a material (among those referred to above) which is resistant to the halogen-bearing bath at the temperature in question (for example a cryolite bath at 980° C.). A particularly advantageous arrangement of the electrodes comprises using a counter-electrode in the form of an open cylinder of graphite, the lower part (for example half) of which is perforated with holes to provide for circulation of the electrolyte or the layer of liquid aluminium. The reference electrode is formed by an internal cylinder of tungsten gauze or mesh which is concentric with the graphite counter-electrode and without contact therewith. The indicator electrode is preferably formed by a graphite rod disposed substantially along the common axis of the counter-electrode and the reference electrode. The position of the graphite rod may preferably be so adjusted that its lower end just reaches the level or a little above the level of the lower perforated region of the graphite counter-electrode so that the circulating currents in the halogen-bearing bath bring the oxide ions to the vicinity thereof without interfering with the diffusion layer.

It is possible to add an external screen which is for example of graphite and which is connected to a fixed potential in order to protect the three electrodes from parasitic electrical fields. The graphite counter-electrode may also perform that protective function.

Finally, in some cases, it is possible for the counter-electrode and the reference electrode to be combined in a single electrode.

The reference electrode can be immersed in a molten salt disposed in a separate compartment which is in electrical communication with the main molten bath.

After the electrodes have been set in position and the temperature of the molten halogen-bearing bath has been checked, the internal potentiostat of the generator is regulated so as to apply to the indicator electrode a d.c. overvoltage of +10 to +800 mV and preferably +400 to +600 mV with respect to its zero-current rest potential (which is determined by means of the reference electrode).

If the electrochemical reaction at the indicator electrode gives rise to the production of gas (for example $CO/CO_2$ if it consists of carbon), it is necessary to limit the anodic current density to less than 10% and preferably less than 2% of the diffusion-limit current density, both to avoid modifications to the surface of the electrode (by virtue of combustion in the case of carbon) and interference with the measurements due to gas bubbles being produced.

Then the periodic signal generator (for example for a sinusoidal output signal) is regulated so as to superimpose on the potential of the indicator electrode a signal at a low amplitude (1 to 100 mV and preferably 5 to 20 mV peak-to-peak) by sweeping in a decreasing mode a range of frequencies of $10^5$ to 0.5 Hz in logarithmic steps. The signal resulting from the system of electrodes is picked up at the terminals of an aselfic resistor (non-inductive) of very low value (for example 10 m$\Omega$) which is disposed in the circuit between the counter-electrode and the indicator electrode; that signal is analysed by one of the methods which are well known to the man skilled in the art (for example synchronous detection or by means of a Wheatstone bridge) in such a way as to determine, for each frequency, the real value (Zr) and the imaginary value (−Zi) of the impedance. Those values are set out in a Nyquist diagram.

A particular curve is obtained for each level of concentration of oxide ions in the bath at a given temperature.

FIG. 1, in its lower part, represents an array of six impedancemetric curves in the particular case of a molten cryolite bath at 980° C. comprising 83% of cryolite ($Na_3AlF_6$), 12% of aluminium trifluoride ($AlF_3$) and 5% of calcium difluoride ($CaF_2$), in which alumina is dissolved, the concentration of alumina increasing when going from curve 1 to curve 6:

1—0.50% $Al_2O_3$
  2—0.97% $Al_2O_3$
  3—1.20% $Al_2O_3$
  4—1.46% $Al_2O_3$
  5—1.91% $Al_2O_3$
  6—12.0% $Al_2O_3$ curve 6, at 12.0% of $Al_2O_3$ practically corresponding to saturation of the bath in respect of $Al_2O_3$.

It is found that, the lower the level of concentration of oxide ions, the larger the area defined by the curve, which gives the method a high level of sensitivity in the range of low levels of concentration (0.5 to 4% by weight) of dissolved alumina.

In addition it is found that, in a frequency range of from 0.5 to 50 Hz, the different curves intersect the axis of the real values with a practically vertical tangent and that, in the vicinity of that axis, the degree of curvature of each curve is low, which means that in that frequency range the real part of the impedance Zr(B) is practically constant.

At high frequency, for example beyond $10^3$ Hz, the real part of the impedance (Zr(H) varies very little under the specified operating conditions and practically depends only on the ohmic conductors of the assembly of the measuring circuit including the molten bath itself, the conductivity of which varies substantially in dependence on the level of concentration of oxide ions.

For each concentration of ions $O^{-II}$, if now the inverse of the level of concentration C of ions $O^{-II}$ in dependence on the difference ΔZ (in ohms) between Zr(B) and Zr(H) is plotted on a graph, the result is a practically linear calibration curve. The following can be written, with a very good degree of approximation:

$$C(O^{-II}) = \frac{A}{\Delta Z - B}$$

C being expressed in moles of ions $O^{-II}.cm^{-3}$,

A and B being constants which are determined by a preliminary calibration operation, B being generally equal to O, in the case shown in FIG. 1.

In regard to the different levels of concentration of alumina indicated, the upper part of FIG. 1 shows the real part of the impedance ΔZr in the abscissae and the inverse of the concentration of ions $O^{-II}$ (in $10^{-3}.mol^{-1}.cm^3$), in the ordinates.

It is easy to see from those calibration curves that if the impedance values are in the vicinity of the points Zr(H) and Zr(B), it is possible to link directly the difference in the real parts of such impedances to the level of concentration of alumina.

In practice, by effecting a first measurement or preferably a series of measurements from which the average is taken, carried out at a frequency of higher than 1000 Hz but preferably higher than 10 kHz, and a measurement (or a series of averaged measurements) at a frequency of between 0.5 and 50 Hz and preferably between 15 and 25 Hz, it is possible, from the real values of the impedance at high frequency and at low frequency which are obtained under those conditions and which are very good estimations of Zr(B) and Zr(H), to deduce the level of concentration of alumina or other dissolved oxide, without having to sweep through the whole of the frequencies curve.

EXAMPLES OF USE

The invention was carried into effect in the particular case of an electrolysis bath of the Hall-Heroult type for the production of aluminium, comprising 83% of Na$_3$AlF$_6$+12% of AlF$_3$+5% of CaF$_2$, at 980° C.

The impedance measurements were made by means of the apparatus "Z-Computer" from Ets TACUSSEL, connected to a HP.9826 microcomputer from HEWLETT-PACKARD.

EXAMPLE 1

The apparatus used in this example is shown schematically in FIG. 1.

An amount of bath of the order of 250 g, composed of 83% of natural Greenland cryolite, 5% of calcium fluoride and 12% of bisublimated aluminium fluoride, is prepared. The bath is previously dried in a drying oven at 300° C. and then placed in a crucible 6 which is heated in oven 7 to a temperature of 980° C. in an argon atmosphere and protected by a Faraday cage which is connected to earth. Using a graphite tube, thionyl chloride is bubbled into the liquefied bath in order to provide for as complete elimination as possible of any residual oxide ions which may be present in the starting raw materials.

The following are then dipped into the bath:

a known reference electrode 1 formed by a nickel bar of a diameter of 1 mm, which extends into a compartment 6a of boron nitride, apertured by laser with a micro-hole of a diameter of 100 mm, in which there is a bath of the same composition as the main bath but to which 0.5% of nickel oxide is added;

a second reference electrode 2 formed by a tungsten bar of a diameter of 2 mm, which dips directly into the molten bath 5;

an indicator electrode 3 of industrial graphite which is machined at its tip, of a diameter of 3 mm, and a tungsten blade 4 which has an area of contact with the bath of 20 cm2.

The electrodes 1 and 2 are connected to the terminals of a millivoltmeter 8 with a very high input impedance, associated with a recording device 9, while the electrodes 2, 3 and 4 are connected to the corresponding terminals of the impedancemeter 10.

A first charge of alumina which has been weighed beforehand is dropped into the bath and the generator is programmed so as to apply to the indicator electrode an overvoltage of 550 mV relative to its equilibrium point. Superimposed on its potential is then a series of sinusoidal signals of peak-to-peak amplitude of 10 mV and, by synchronous detection, the current is then analysed so as to plot the real part and the imaginary part of the impedance, in the falling and then the rising direction, for each frequency.

Those values are plotted on a Nyquist diagram.

At the end of the sweep operation, a sample is taken at the heart of the bath to provide for quantitative determination in accordance with a conventional method (dissolution in AlCl$_3$) of the real amount of alumina which is compared to the calculated amount, with the mass of the bath and the weight of the amount added being known.

That operation is effected for 5 successive addition steps. The Nyquist diagrams obtained after smoothing out the singular points are represented in the lower part of FIG. 1.

Then, plotted on another diagram (upper part of FIG. 1), for each addition step, are points whose abscissae are the value ΔZr=Max.(Zr)−Min (Zr), (Max(Zr) and Min (Zr) representing the extreme values of the real part of the impedance for each curve) and whose ordinates are the inverse of the concentration of oxide ions as measured by an analytical procedure expressed as $10^{-3}$ moles$^{-1}$ of ions $O^{-II}.cm^3$.

That gives a practically linear calibration curve which by smoothing leads to the following relationship:

$$C\text{(in moles} \cdot \text{cm}^3) = \frac{9.4 \times 10^{-4}}{\Delta Zr\text{(in }\Omega\text{)}}$$

Since 1 mole of alumina by total dissolution gives 3 moles of ions $O^{-II}$, since the molar weight of alumina is 102 g and since the mass in relation to volume of the bath under the conditions of the measurement operation is 2.03 g.cm$^{-3}$, it is easily deduced therefrom that:

$$C\text{(in \% by weight of alumina)} = \frac{1.57}{\Delta Zr\text{(in }\Omega\text{)}}$$

It is also verified in parallel therewith that:
the recording of the voltage at the terminals of the electrodes 1 and 2 remains stable, which means that the electrode 2 which is formed by a simple tungsten bar immersed in the bath is indeed a stable reference electrode, there is a good correspondance between the levels of concentration forecast on the basis of the weighing operations and the values obtained in the analysis procedure, and the values of Zr obtained in a range of frequencies of 0.5 to 50 Hz are close to Max(Zr) and those obtained for frequencies of higher than 1000 Hz are close to Min(Zr) and can therefore be respectively assimilated to Max(Zr) and Min(Zr).

It can be observed at the end of the experiment that a very substantial amount of alumina added to the bath results in the formation of a minute loop which according to the calibration operation corresponds to an amount of close to 12% by weight, that is to say the equilibrium value close to saturation.

EXAMPLE 2

The methodology of Example 1 can be used for rapidly determining the mechanism involved in dissolution of an industrial alumina. For that purpose, the same type of bath as previously is used (cryolite=83%, $CaF_2$=5%, $AlF_3$=12%, temperature 980° C. and the same heating apparatus).

The reference electrode is formed by the same tungsten bar while the indicator electrode is also a bar of industrial graphite which is machined at the end with a diameter of 3 mm, with the graphite crucible acting as the counter-electrode.

The electrodes are connected to the terminals of the impedancemeter and the overvoltage at the graphite electrode is fixed at the same value of 550 mV.

Two base frequencies of $10^4$ Hz and 21 Hz are set. The 10 mV signal corresponding to those two frequencies is superimposed on the potential of the indicator.

Measurements are then made in the following fashion:

signal at $10^4$ Hz: acquisition of $Zr(10^4)$
signal at 21 Hz: acquisition of $Zr(21)$ $$\text{automatic calculation of } C = \frac{1.57}{Zr(21) - Zr(10^4)}$$

plotting of the point on a diagram concentration in dependence on time C=f(t).

An amount of alumina in the form of a "cigarette" which is disposed at the surface of the bath is then added and the previous cycle is begun again in a continuous procedure.

Figure 2:
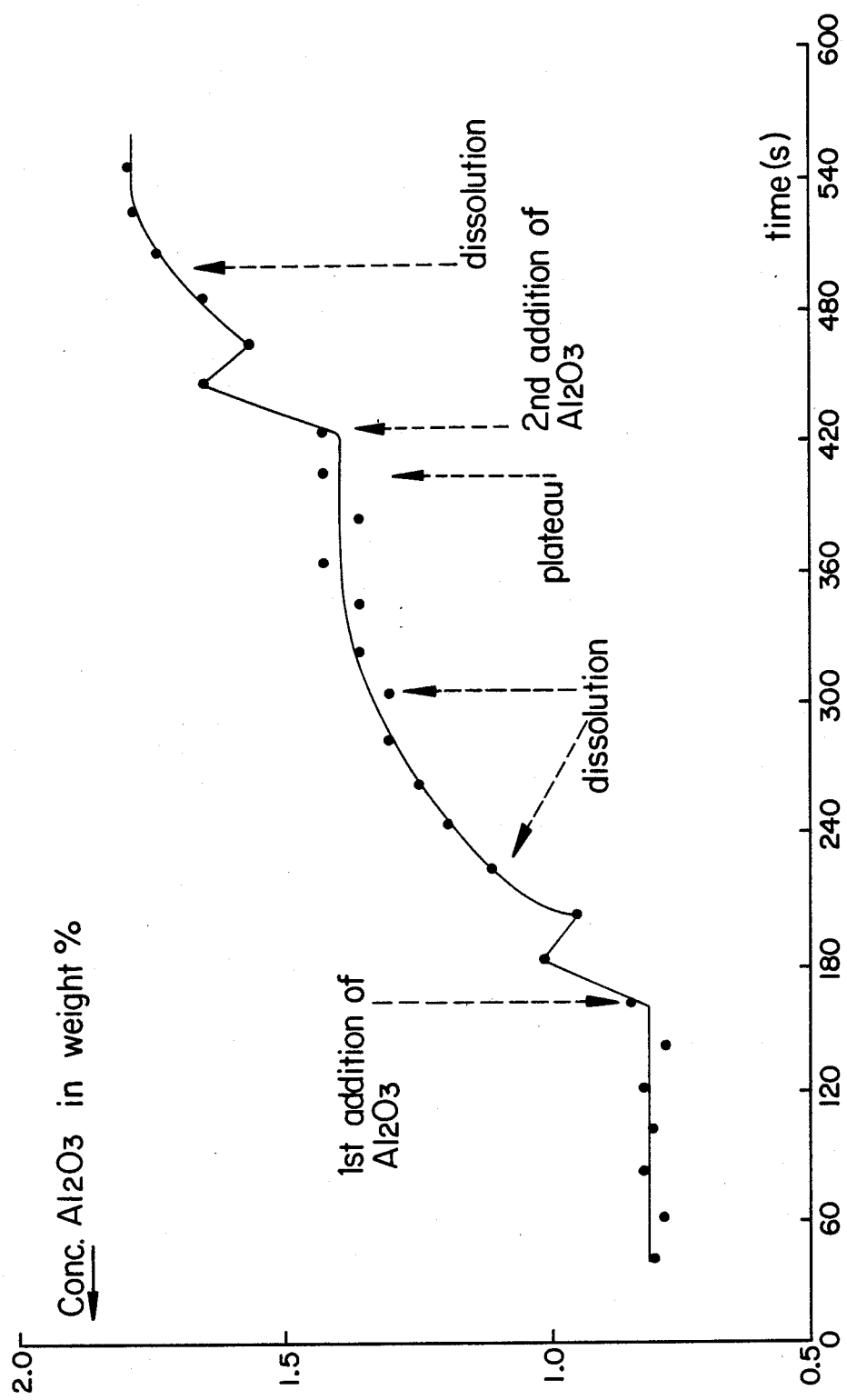
FIG. 2 is a plot of alumina concentration versus time for the system described in Example 2.
Figure 3:
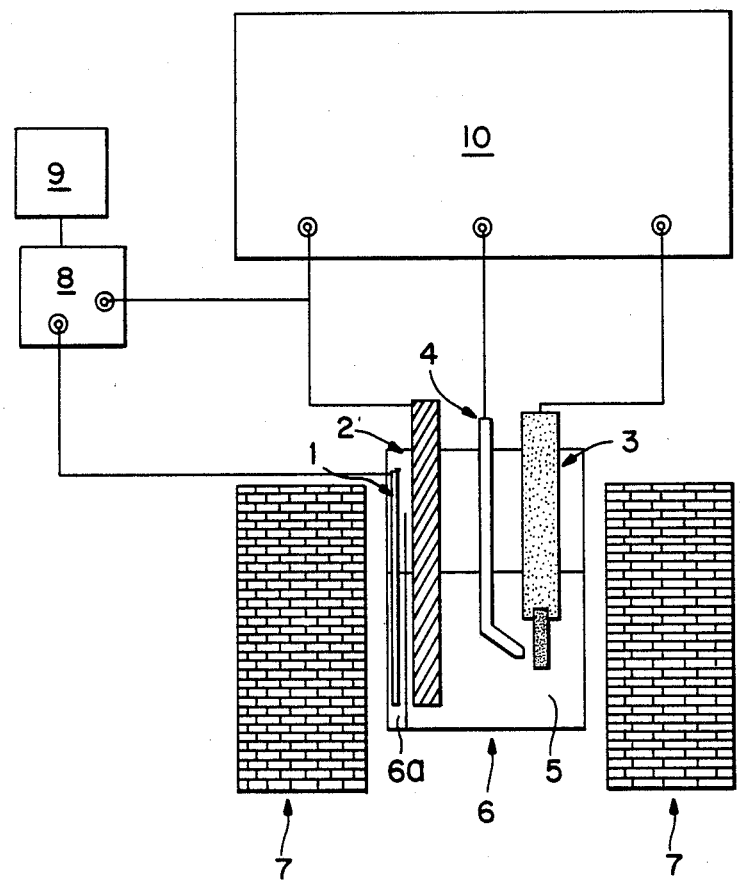
FIG. 3 is a schematic diagram of the apparatus and in Example 1.

That then gives on the diagram C=f(t): (FIG. 2):
a plateau corresponding to the steady-state phase before any addition of alumina (detection of residual oxides), a narrow peak corresponding to the disturbance resulting from the addition of alumina, a progressive rise linked to dissolution of the alumina (solid oxide) in the molten bath, producing oxide ions $O^{-II}$. The faster that rise, the higher the rate of dissolution;

a stabilisation phase (plateau) when all the alumina is dissolved.

If desired it is possible to carry out a number of addition operations at regular periods of time. However it is the first addition (low levels of concentration) which best represents the phenomena observed when supplying modern industrial tanks for the production of aluminium.

EXAMPLE 3

The proposed impedancemetric apparatus is used as an alumina probe in an industrial aluminium electrolysis tank. It is found in fact that the tanks use as the electrolyte a bath of a composition close to that described in the foregoing Examples.

In this case the indicator electrode is formed by the same graphite bar as above. The reference electrode is a tungsten gauze surrounding the graphite bar at a distance of 1 cm. The counter-electrode is a perforated tungsten cylinder at the potential of the layer of liquid aluminium with which it will be covered.

The electrodes are connected to the impedancemeter and the same overvoltage of 550 mV is again applied to the indicator electrode. There is then superimposed on the potential of the indicator electrode a succession of sinusoidal signals of an amplitude of 10 mV with frequencies varying from 6 Hz to 43 Hz in a decreasing and then an increasing order. That operation is repeated 5 times.

For each frequency used, the real value of the impedance is determined. A calculation programme makes it possible to carry out statistical analysis of the results, to ascertain the average, the confidence range, and to detect aberrant values linked to electrical interference or noise. Scrutation is then effected at the high frequencies $10^3$ Hz, $3 \times 10^3$ Hz, $10^4$ Hz, $3 \times 10^4$ Hz, $10^5$ Hz, and the same statistical treatment is carried out.

Then, for calculation purposes, use is made of the mean values of Zr for the low frequencies $\overline{Zr(B)}$ and the high frequencies $\overline{Zr(H)}$.

The level of concentration of alumina in the electrolyte in the tank at the measurement point is given in accordance with the calibration curve by:

$$C\ (\% \text{ by weight}) = \frac{1.57}{Zr(B) - Zr(H)}$$

Use of the invention makes it possible to monitor and therefore regulate in a permanent mode the amount of alumina in Hall-Heroult electrolysis tanks for the production of aluminium and in particular modern tanks of point feed type, operating with a very small amount of alumina, of the order of 1 to 3.5%, which are to be regulated in a highly accurate fashion in order to optimise the Faraday efficiency.

By multiplexing of the signals, it is possible permanently to ascertain the real amount of $Al_2O_3$ in the electrolyte in each tank and to introduce that parameter into the central computer and/or into the local microprocessor which provides for regulation of the tank (alumina feed rate, anode-cathode distance, treatment in respect of instabilities, etc . . . ).

We claim:

1. Process for electrochemical measurement of the concentration of oxide ions in a bath based on molten halide characterised by effecting impedancemetry with a low current and a low overvoltage, comprising the steps of:

disposing an indicator electrode, a reference electrode and a counter-electrode in the bath based on molten halide, applying a potential difference between the indicator electrode and the reference electrode so that the indicator electrode is the location of an anodic electrochemical reaction and the counter-electrode is the location of a cathodic electrochemical reaction, if the electrochemical reaction a the indicator electrode gives rise to the production of gas, adjusting said potential difference so as to obtain an anodic current density at most equal to 10% of the diffusion limit current density corresponding to the oxide ions in the bath, superimposing a periodic signal of adjustable frequency and low amplitude on the potential of the indicator electrode, determining the real value Zr(H) of the impedance at a first high frequency at least equal to 1000 Hz and the real value Zr(B) of the impedance at a second low frequency which is lower than 50 Hz, calculating the proportion of oxide ions in the bath by applying the relationship:

$$C(O^{-II}) = \frac{A}{\Delta Zr - B}$$

$\Delta Zr$ being equal to $Zr(H) - Zr(B)$, A and B being constants obtained by preliminary calibration.

2. A process according to claim 1 wherein an overvoltage is applied to the indicator electrode of between 10 and 800 mV with respect to its zero-current rest potential and is determined by means of the reference electrode.

3. A process according to claim 2, wherein said overvoltage applied to the indicator electrode is between 400 and 600 mV.

4. A process according to claim 1 or claim 2 wherein the amplitude of the periodic signal is between 1 and 100 mV peak-to-peak.

5. A process according to claim 4, wherein the amplitude of the periodic signal is between 5 and 20 mV peak to peak.

6. A process according to claim 1 wherein the periodic signal is sinusoidal.

7. A process according to claim 1 wherein the high frequency is at least equal to 10 kHz.

8. A process according to claim 1 wherein the low measuring frequency is between 0.5 and 50 Hz.

9. A process according to claims 1, 7 or 8 wherein, for each high and low frequency, a plurality of measurements are made and the average thereof is taken.

10. A process according to claim 7, wherein the high frequency is between 10 kHz and 100 kHz.

11. A process according to claim 8, wherein the low frequency is between 15 and 25 Hz.

12. Process according to claim 1 further comprising quantitative determination of the alumina in cryolite baths for the production of aluminium using the Hall-Heroult process and the oxides dissolved in halogen-bearing baths for the electrolytic production of metals in the rare earth group.

13. Process according to claim 1 further comprising measuring the rate of dissolution of the alumina in cryolite baths for the production of aluminium using the Hall-Heroult process.

14. A process according to claim 1, wherein said anodic current density is at most equal to 2% of the diffusion limit current density corresponding to the oxide ions in the bath.

* * * * *